(12) United States Patent
Chen (10) Patent No.: US 11,980,909 B2
(45) Date of Patent: May 14, 2024

(54) THREE-DIMENSIONAL ATOMIZATION DEVICE FOR HEATING A POROUS LIQUID GUIDING MATERIAL

(71) Applicant: Shenzhen Huachengda Precision Industry Co. Ltd., Guangdong (CN)

(72) Inventor: Ping Chen, Guangdong (CN)

(73) Assignee: Shenzhen Huachengda Precision Industry Co. Ltd., Shenzhen (CN)

( * ) Notice: Subject to any disclaimer, the term of this patent is extended or adjusted under 35 U.S.C. 154(b) by 840 days.

(21) Appl. No.: 17/059,248

(22) PCT Filed: Feb. 14, 2019

(86) PCT No.: PCT/CN2019/075095
§ 371 (c)(1),
(2) Date: Nov. 26, 2020

(87) PCT Pub. No.: WO2020/151035
PCT Pub. Date: Jul. 30, 2020

(65) Prior Publication Data
US 2021/0205827 A1    Jul. 8, 2021

(30) Foreign Application Priority Data

Jan. 25, 2019  (CN) .......................... 201910073741.5

(51) Int. Cl.
*B05B 7/16*   (2006.01)
(52) U.S. Cl.
CPC .............. *B05B 7/1613* (2013.01); *B05B 7/16* (2013.01); *B05B 7/1686* (2013.01)

(58) Field of Classification Search
CPC ........... B05B 7/16; B05B 7/1686; B05B 7/22; A61M 11/042; A24F 40/46
(Continued)

(56) References Cited

U.S. PATENT DOCUMENTS

| 2016/0106153 A1* | 4/2016 | Zhu | .......................... A24F 40/46 |
| | | | 392/404 |
| 2020/0367564 A1* | 11/2020 | Li | ........................... A24F 40/44 |

(Continued)

FOREIGN PATENT DOCUMENTS

| CN | 205180364 U | 4/2016 |
| CN | 108185535 A | 6/2018 |

OTHER PUBLICATIONS

International Search Report of PCT Patent Application No. PCT/CN2019/075095 issued on Oct. 24, 2019.

*Primary Examiner* — Jason J Boeckmann (57) ABSTRACT

Provided is a three-dimensional atomization device for heating a porous liquid guiding material. The atomization device comprises a porous liquid guiding material member (10) and a heating member (20). The porous liquid guiding material member (10) has a plurality of outer surfaces. The heating member (20) is provided on at least two adjacent outer surfaces of the plurality of outer surfaces to form at least two heating surfaces (201). The heating member (20) forms one or more metal heating trajectories (100) on the heating surfaces (201). The metal heating trajectories (100) are equidistantly distributed in a lengthwise direction of the porous liquid guiding material member (10). The porous liquid guiding material member (10) realizes a liquid transmission along a lengthwise direction which is defined as a first direction, and an airflow transmission along a second direction which is perpendicular to the second direction.

11 Claims, 7 Drawing Sheets

(58) Field of Classification Search
USPC .................................................. 239/135, 136
See application file for complete search history.

(56) References Cited

U.S. PATENT DOCUMENTS

2022/0287156 A1* 9/2022 Chen ..................... A24F 40/46
2022/0408815 A1* 12/2022 Chen .................... A24F 40/485

* cited by examiner

THREE-DIMENSIONAL ATOMIZATION DEVICE FOR HEATING A POROUS LIQUID GUIDING MATERIAL

TECHNICAL FIELD

The present invention relates to the technical field of atomizers, in particular to a three-dimensional atomization device for heating a porous liquid guiding material.

BACKGROUND

In recent years, atomizers has become more and more popular with wider application. The atomizer may be used, for example, to atomize a liquid medicine for the patient to inhale, or to atomize an essential oil into the air so that the essential oil can be quickly dispersed in the environment, or to atomize water to increase air humidity or reduce ambient temperature. The atomizer may alternatively be used as a watering device for some plants.

At present, there are roughly two heating modes in the atomization devices for heating porous materials in the art, one is to heat at a single surface of the porous liquid guiding material, and the other is to heat at 360 degrees around the porous liquid guiding material. These two heating methods have corresponding disadvantages respectively. The single surface heating method has a small heating area and thus has a low heat utilization rate, and the heat is concentrated on the single surface of the porous liquid guiding material, resulting a local high temperature which may cause the edible liquid to volatilize harmful substances endangering the user's health. In the 360-degree heating mode around the porous liquid guiding material, the aerosol on the back surface of the airflow cannot be discharged by the airflow in time, resulting in a high temperature of the heating trajectory on the porous material at the back surface of the airflow, and thus harmful substances will be volatilized due to the local high temperature, which will harm the health of the user.

SUMMARY

In order to overcome the disadvantages of the prior art, the present invention provides a three-dimensional atomization device for heating a porous liquid guiding material, enabling more sufficient heating, more uniform heat distribution and a larger atomization area.

A technical solution of the present invention adopted to solve the technical problem is to provide a three-dimensional atomization device for heating a porous liquid guiding material, wherein the atomization device includes a porous liquid guiding material member for adsorbing liquid and a heating member for heating and atomizing the liquid adsorbed in the porous liquid guiding material member;

the porous liquid guiding material member has a plurality of outer surfaces, and the heating member is embedded in at least two adjacent outer surfaces of the plurality of outer surfaces to form at least two heating surfaces; the porous liquid guiding material member has at least one outer surface that is not embedded with the heating member; the heating member forms one or more metal heating trajectories on the heating surfaces, and the metal heating trajectory is rectangular wave-shaped;

the porous liquid guiding material member is capable of realizing a liquid transmission along a lengthwise direction which is defined as a first direction, and an airflow transmission along a second direction which is perpendicular to the second direction; the heating surface directly faces the direction in which the airflow flows to the porous liquid guiding material member; a central axis passing through the porous liquid guiding material member is provided along the second direction, and the heating surface is axisymmetric along the central axis.

In the above structure, the rectangular wave-shaped metal heating trajectory is composed of main heating sections, a top connecting section and a bottom connecting section; a plurality of the main heating sections are parallel; the top connecting section is used to connect top ends of two adjacent main heating sections; the bottom connecting section is used to connect bottom ends of two adjacent main heating sections.

In the above structure, among the plurality of the main heating sections of the metal heating trajectory, every two adjacent main heating sections are equidistantly distributed.

In the above structure, among the plurality of the main heating sections of the metal heating trajectory, sectional areas of the main heating sections are stepped or progressive gradually increasing or decreasing from two sides toward a center.

In the above structure, the porous liquid guiding material member is provided with a hollow flow-through hole in the lengthwise direction, and the liquid to be atomized flows through the flow-through hole;

alternatively, the porous liquid guiding material member is provided with an inwardly recessed strip groove in the lengthwise direction, and the liquid to be atomized flows through the strip groove.

In the above structure, a section of the porous liquid guiding material member in a width direction is triangular, trapezoidal or rectangular.

In the above structure, the three-dimensional atomization device for heating a porous liquid guiding material further includes an outer cover and a base; the base covers an opening at one end of the outer cover, and is provided with an air inlet communicating with the inside of the outer cover; the outer cover is provided with an aerosol outlet on the top; an airflow channel is provided between the air inlet and the aerosol outlet;

the porous liquid guiding material member and the heating member are provided in the outer cover; the porous liquid guiding material member is fixed on the base; the porous liquid guiding material member and the heating member are located in the airflow channel; the heating member has a positive terminal and a negative terminal; the base is provided thereon with a first electrode electrically connected with the positive terminal of the heating member and a second electrode electrically connected with the negative terminal of the heating member.

In the above structure, two ends of the porous liquid guiding material member are each fixedly provided with a silicone member, which is provided with an annular groove;

the base is provided thereon with a first convex post facing the porous liquid guiding material member; a cover is provided above the porous liquid guiding material member; the cover is provided with a second convex post facing the porous liquid guiding material member; the first convex post and the second convex post are respectively clamped into the groove of the silicone member.

In the above structure, two ends of the porous liquid guiding material member are respectively provided with an annular protrusion; the silicone member is provided therein with an annular receiving groove; the annular protrusion is clamped in the receiving groove of the silicone member.

In the above structure, the cover is provided with a through hole and a silicone cover; the silicone cover is provided thereon with a connection hole extending outward; the connection hole communicates with the aerosol outlet of the outer cover.

The three-dimensional atomization device for heating a porous liquid guiding material provided by the present invention has the following beneficial effects: the atomization device makes full use of space, and embeds metal heating trajectories in the surfaces of the porous liquid guiding material member on the airflow sides, and has the beneficial effects of making heating more sufficient, making the amount of heat more uniform, making the atomization area larger, and making the amount of the atomized aerosol larger, and can generate a relatively large amount of atomized aerosol in a relatively small space.

BRIEF DESCRIPTION OF THE DRAWINGS

FIG. 1 shows a first embodiment of a porous liquid guiding material member and a heating member of a three-dimensional atomization device for heating a porous liquid guiding material according to the present invention.

FIG. 2 shows a second embodiment of the porous liquid guiding material member and the heating member of the three-dimensional atomization device for heating a porous liquid guiding material according to the present invention.

FIG. 3 shows a third embodiment of the porous liquid guiding material member and the heating member of the three-dimensional atomization device for heating a porous liquid guiding material according to the present invention.

FIG. 4 shows a fourth embodiment of the porous liquid guiding material member and the heating member of the three-dimensional atomization device for heating a porous liquid guiding material according to the present invention.

FIGS. 5 and 6 respectively show an embodiment of a metal heating trajectory of the three-dimensional atomization device for heating a porous liquid guiding material according to the present invention.

FIG. 7 shows a fifth embodiment of the porous liquid guiding material member and the heating member of the three-dimensional atomization device for heating a porous liquid guiding material according to the present invention.

FIG. 8 shows a sixth embodiment of the porous liquid guiding material member and the heating member of the three-dimensional atomization device for heating a porous liquid guiding material according to the present invention.

FIG. 9 shows an embodiment of the three-dimensional atomization device for heating a porous liquid guiding material according to the present invention.

FIG. 10 is an exploded view of the embodiment of the three-dimensional atomization device for heating a porous liquid guiding material according to the present invention.

FIG. 11 shows a structural diagram of the porous liquid guiding material member, the heating member and a silicon part of the three-dimensional atomization device for heating a porous liquid guiding material according to the present invention.

DETAILED DESCRIPTION

The present invention is described in more detail with reference to the accompanying drawings and embodiments.

In order to make the objectives, features and effects of the present invention fully understood, the concepts, specific structures and technical effects of the present invention are clearly and completely described below in conjunction with the embodiments and drawings. Apparently, the described embodiments are merely a part rather than all of the embodiments of the present invention. All other embodiments obtained by those skilled in the art based on the embodiments of the present invention without creative efforts should fall within the protection scope of the present invention. In addition, all the connection relations involved in the present invention do not only refer to the direct connection of the components, but refer to the fact that a better connection structure may be formed by adding or reducing connection accessories according to specific implementation conditions. The various technical features created by the present invention can be combined interactively under the premise of not conflicting with each other.

Referring to FIGS. 1 to 4, the present invention provides a three-dimensional atomization device for heating a porous liquid guiding material. Specifically, the atomization device includes a porous liquid guiding material member 10 for adsorbing liquid and a heating member 20 for heating and atomizing the liquid adsorbed in the porous liquid guiding material member 10. The porous liquid guiding material member 10 has a plurality of outer surfaces, and the heating member 20 is embedded in at least two adjacent outer surfaces of the plurality of outer surfaces to form at least two heating surfaces 201. It should be noted that the porous liquid guiding material member 10 has at least one outer surface that is not embedded with the heating member 20. In an embodiment shown in FIG. 1, a longitudinal section of the porous liquid guiding material member 10 is square; the heating member 20 is provided on three adjacent outer surfaces of the porous liquid guiding material member 10 to form three adjacent heating surfaces 201; a back surface directly opposite to an airflow direction is an outer surface that is not embedded with the heating member 20. In an embodiment shown in FIG. 2, the longitudinal section of the porous liquid guiding material member 10 is a rectangle with a chamfer; the heating member 20 is provided on five adjacent outer surfaces of the porous liquid guiding material member 10 to form five adjacent heating surfaces 201, including three flat surfaces and two arc-shaped surfaces. In an embodiment shown in FIG. 3, the longitudinal section of the porous liquid guiding material member 10 is a triangle; the heating member 20 is provided on two adjacent outer surfaces of the porous liquid guiding material member 10 to form two adjacent heating surfaces 201. In an embodiment shown in FIG. 4, the longitudinal section of the porous liquid guiding material member 10 is a trapezoid; the heating member 20 is provided on three adjacent outer surfaces of the porous liquid guiding material member 10 to form three adjacent heating surfaces 201.

Further, the heating member 20 forms one or more metal heating trajectories on the heating surfaces 201. The metal heating trajectory is in a rectangular wave shape. With such structural design, when the metal heating trajectory heats the porous liquid guiding material member 10, it can ensure uniform heating of each part of the porous liquid guiding material member 10, enabling more uniform heat distribution and a better heating effect.

As shown in FIG. 5, the present invention provides a specific embodiment of the metal heating trajectory 100. In this embodiment, the rectangular wave-shaped metal heating trajectory 100 is composed of main heating sections 1001, a top connecting section 1002 and a bottom connecting section 1003. A plurality of the main heating sections 1001 are parallel. The top connecting section 1002 is used to connect top ends of two adjacent main heating sections 1001. The bottom connecting section 1003 is used to connect bottom ends of two adjacent main heating sections 1001. The top connecting section 1002 is parallel to the bottom connecting section 1003. Further, in this embodiment, among the plurality of the main heating sections 1001 of the metal heating trajectory, every two adjacent main heating sections 1001 are equidistantly distributed. In this way, when the heating member generates heat, the heat spreads along the metal heating trajectory. Through this structure of the metal heating trajectory, the heat dissipation can be realized more uniformly, the uniformity of the temperature can be ensured, the full utilization of the heat can be realized, and the heating effect can be improved.

Figure 1:
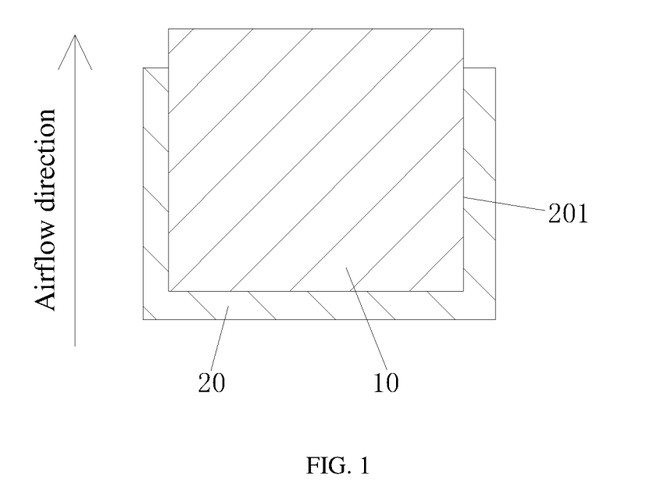
Figure 2:
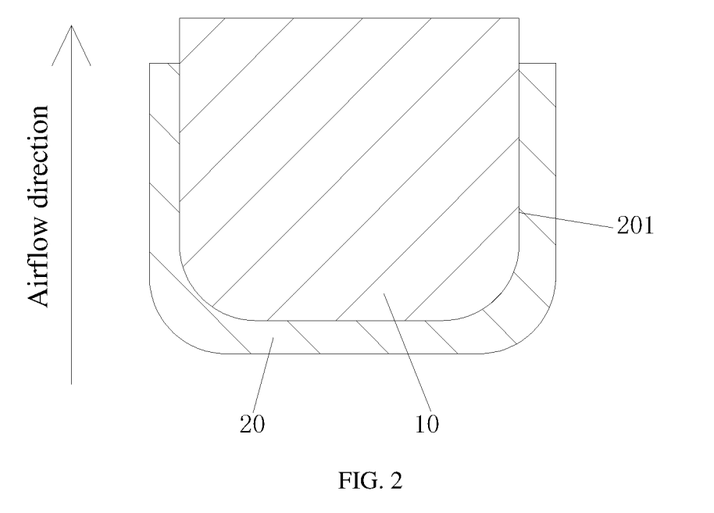
Figure 3:
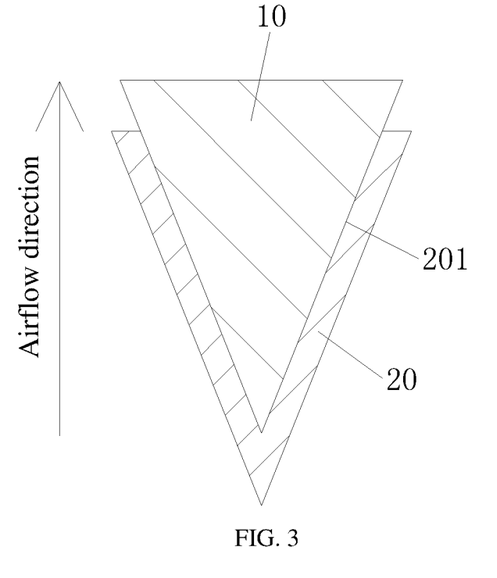
Figure 4:
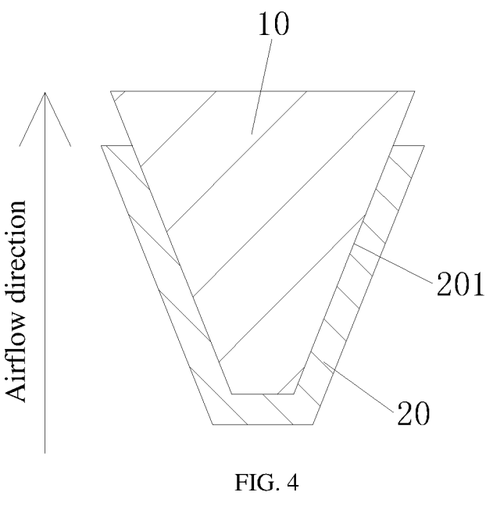
Figure 5:
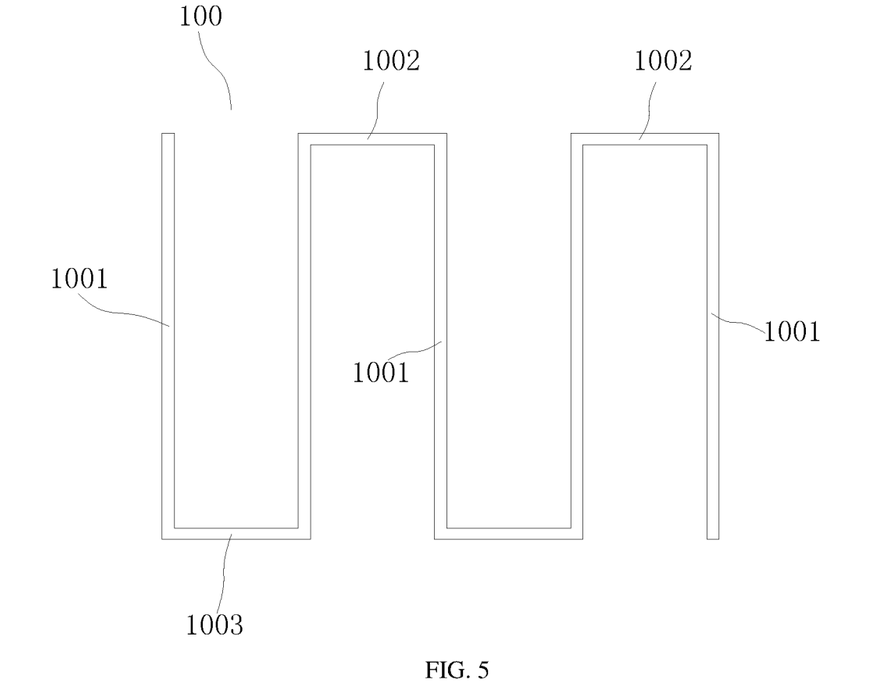
Figure 6:
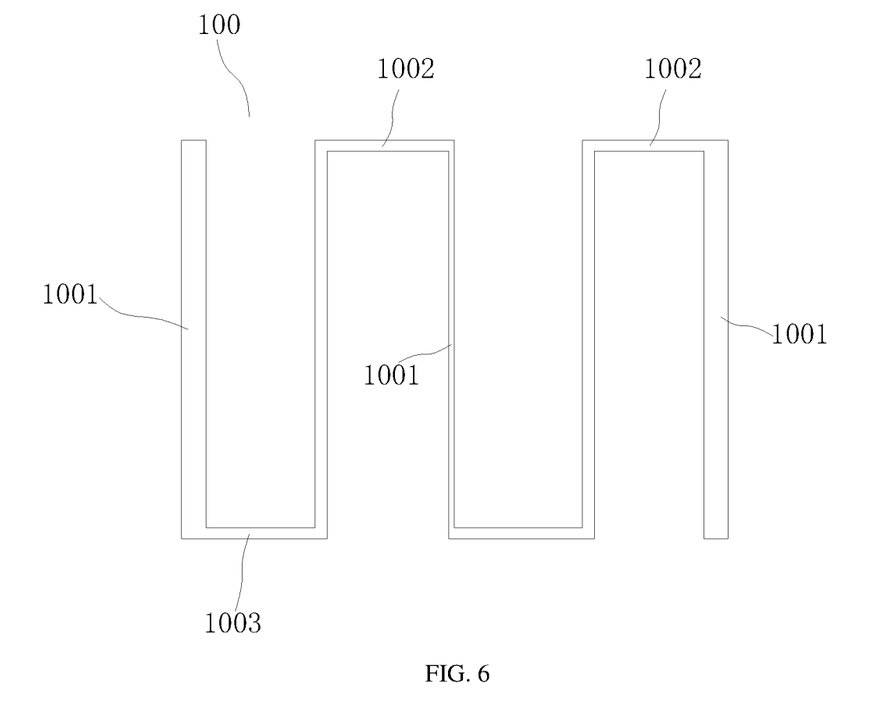

As shown in FIG. 6, on the basis of the embodiment shown in FIG. 5, the present invention further provides an embodiment of the metal heating trajectory. Among the plurality of the main heating sections 1001 of the metal heating trajectory, sectional areas of the main heating sections 1001 are stepped or progressive gradually decreasing from two sides toward a center. It is understandable that the plurality of the main heating sections 1001 are connected in series in a same circuit. When the sectional areas of the main heating sections 1001 decrease, the heat generated within the same time increases. In this way, the metal heating trajectory heats different positions of the porous liquid guiding material member 10 at different temperatures, so as to achieve the requirement of local temperature difference, and expand the application field of the product. It should be noted that as an alternative embodiment, among the plurality of the main heating sections 1001 of the metal heating trajectory, the sectional areas of the main heating sections 1001 are stepped or progressive gradually increasing from two sides toward a center. The change of the sectional areas of the main heating sections 1001 may be adjusted according to actual needs.

Figure 7:
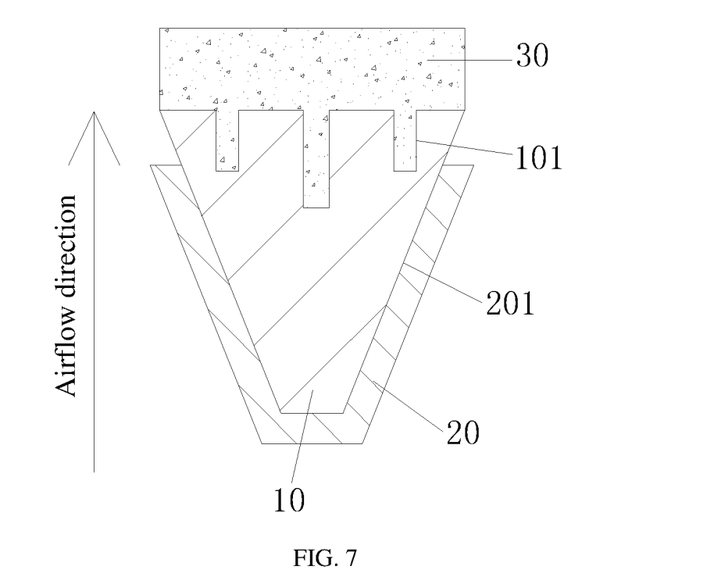
Figure 8:
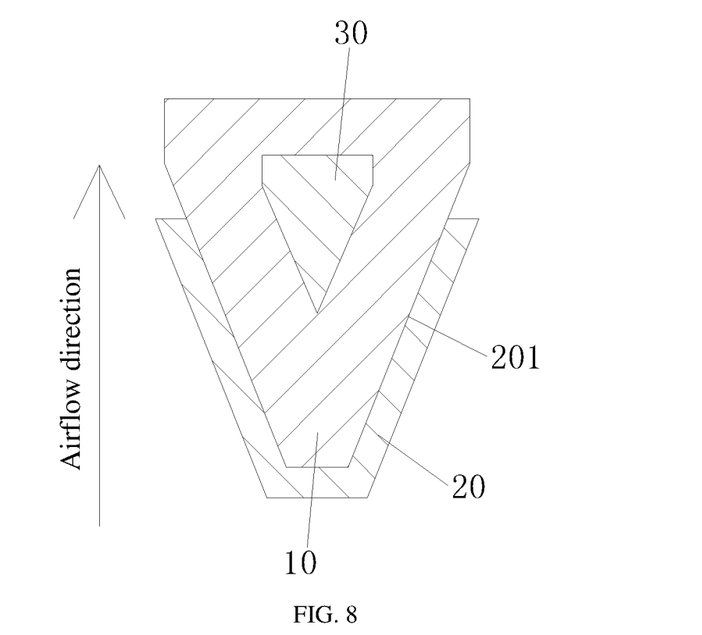

In the above embodiment, the porous liquid guiding material member 10 realizes a liquid transmission in a lengthwise direction which is defined as a first direction, and realizes an airflow transmission in a second direction of the porous liquid guiding material member 10. The first direction is perpendicular to the second direction. The heating surfaces 201 directly face the direction in which the airflow flows to the porous liquid guiding material member 10. The porous liquid guiding material member 10 is provided with a central axis along the second direction. The heating surface 201 is axisymmetric along the central axis. As shown in FIG. 7, in an embodiment provided by the present invention, the porous liquid guiding material member 10 is provided with an inwardly recessed strip groove 101 in the lengthwise direction, and the liquid 30 to be atomized flows through the strip groove 101. The direction of the strip groove 101 is the first direction. In this embodiment, the strip groove 101 is as wide as 0.5 mm or above. In FIG. 7, the airflow direction is the second direction. It can be understood that the porous liquid guiding material member 10 has a symmetrical central axis in the lengthwise direction, and the heating surface 201 is axisymmetric along the central axis. As shown in FIG. 8, the present invention provides a second embodiment of the porous liquid guiding material member 10. This embodiment differs from the above embodiment in that the porous liquid guiding material member 10 is provided with a hollow flow-through hole in the lengthwise direction, and the liquid to be atomized flows through the flow-through hole.

In the above embodiment, when the liquid to be atomized flows, the porous liquid guiding material member 10 adsorbs the liquid. The heating member 20 generates heat, and the heating trajectory provided on the heating surface 201 heats the porous liquid guiding material member 10. The liquid is atomized on the porous liquid guiding material member 10. Since the heating surfaces 201 are facing the direction of the airflow to the porous liquid guiding material member 10, the aerosol is able to be discharged in time by the airflow without being stagnated. This can avoid the problem of a harmful substance volatilized in the porous liquid guiding material member 10 due to local high temperature.

Figure 9:
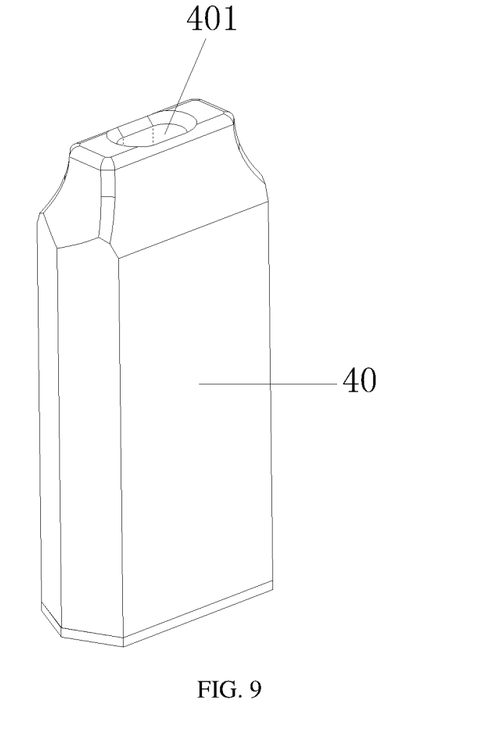
Figure 10:
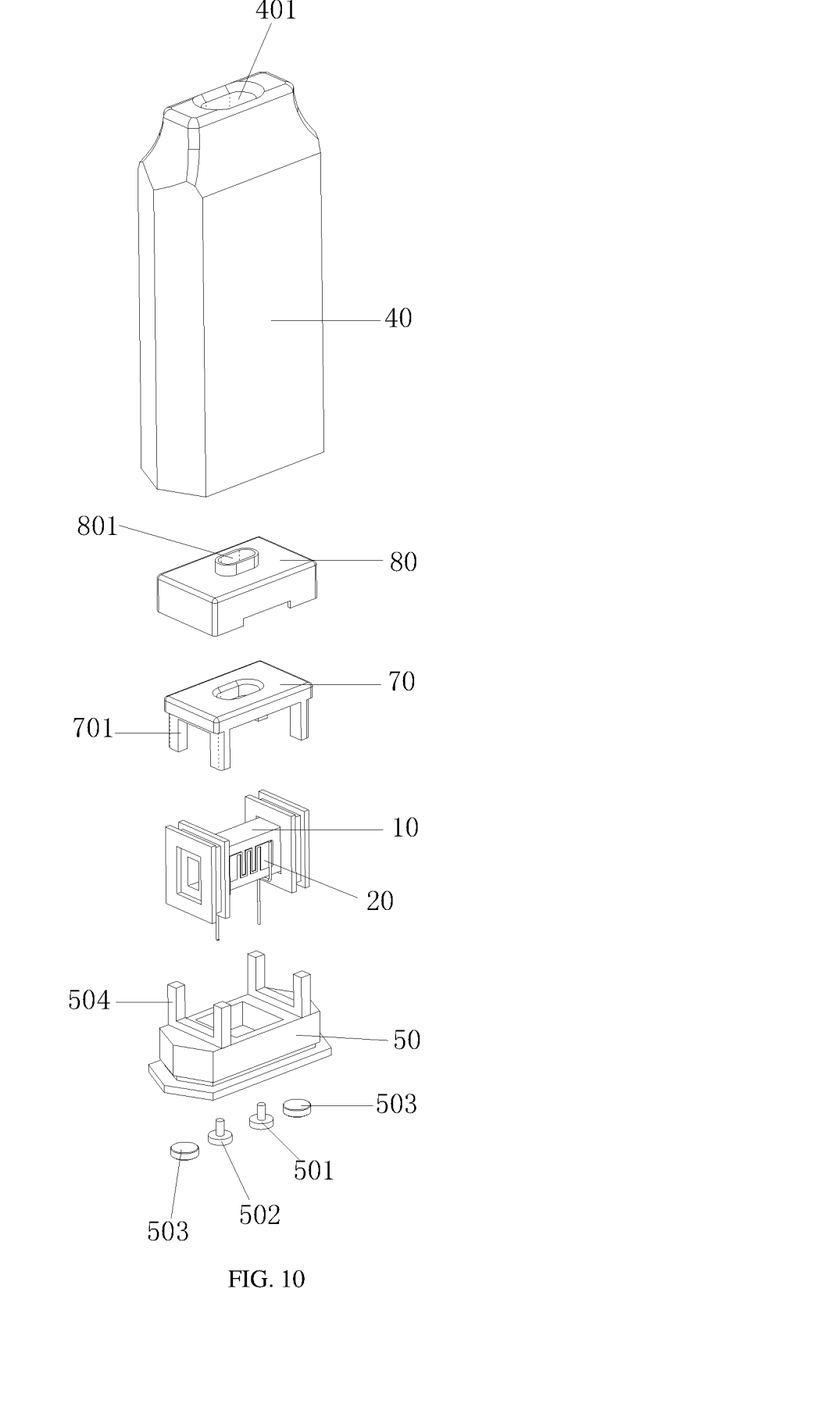
Figure 11:
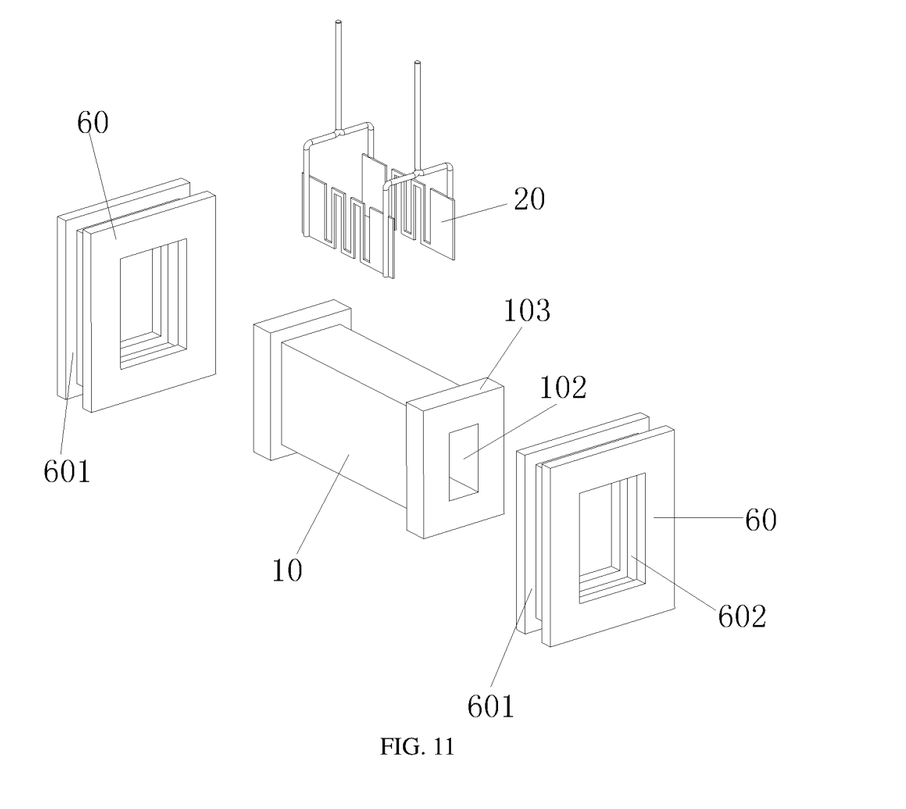

The present invention provides a specific embodiment of the three-dimensional atomization device for heating a porous liquid guiding material based on the above embodiment. As shown in FIGS. 9 to 11, the atomization device further includes an outer cover 40 and a base 50. The base 50 covers an opening at one end of the outer cover 40, and is provided with an air inlet communicating with the inside of the outer cover 40. The outer cover 40 is provided with an aerosol outlet 401 on the top. The porous liquid guiding material member 10 and the heating member 20 are provided in the outer cover. The porous liquid guiding material member 10 is fixed on the base 50. The heating member 20 has a positive terminal and a negative terminal. The base 50 is provided thereon with a first electrode 501 electrically connected with the positive terminal of the heating member 20 and a second electrode 502 electrically connected with the negative terminal of the heating member 20. When the first electrode 501 and the second electrode 502 are electrically connected, the heating member generates heat. Further, the base 50 is provided thereon with magnets 503.

Further, as shown in FIG. 11, the porous liquid guiding material member 10 is in a rectangular parallelepiped shape, and a rectangular parallelepiped flow-through hole 102 is provided in the lengthwise direction. Two ends of the porous liquid guiding material member 10 are each fixedly provided with a silicone member 60, which is provided therein with an annular groove 601. The base 50 is provided thereon with first convex posts 504 facing the porous liquid guiding material member 10. A cover 70 is provided above the porous liquid guiding material member 10. The cover 70 is provided with second convex posts 701 facing the porous liquid guiding material member 10. The first convex posts 504 and the second convex posts 701 are clamped into the groove 601 of the silicone member 60 respectively. Two ends of the porous liquid guiding material member 10 are respectively provided with an annular protrusion 103. The silicone member 60 is provided therein with an annular receiving groove 602. The annular protrusion 103 is clamped in the receiving groove 602 of the silicone member 60. In this way, the porous liquid guiding material member 10 is fixed. Meanwhile, the two ends of the porous liquid guiding material member 10 are sealed to prevent the airflow from leaking from the two ends of the porous liquid guiding material member 10, and to ensure that the airflow enters via the direction of the base 50 and flows out via the through hole of the cover 70. Further, the cover 70 is provided thereon with a silicone cover 80. The silicone cover 80 is provided thereon with a connection hole 801 extending outward. The connection hole 801 communicates with the aerosol outlet 401 of the outer cover 40. The aerosol is discharged with the airflow from the aerosol outlet 401 through the connection hole 801.

The three-dimensional atomization device for heating a porous liquid guiding material provided by the present invention makes full use of space, and embeds metal heating trajectories on the surfaces of the porous liquid guiding material member 10 on the airflow sides. The atomization device has the beneficial effects of making heating more sufficient, making the amount of heat more uniform, making the atomization area larger, and making the amount of the atomized aerosol larger, and can generate a relatively large amount of atomized aerosol in a relatively small space.

The preferred implementations of the present invention are described in detail above, but the present invention is not limited to the embodiments. Those skilled in the art may make various equivalent modifications or substitutions without departing from the spirit of the present invention, and these equivalent modifications or substitutions are all included in the scope defined by the claims of this application.

What is claimed is:

1. A three-dimensional atomization device for heating a porous liquid guiding material, comprising a porous liquid guiding material member for adsorbing liquid and a heating member for heating and atomizing the liquid adsorbed in the porous liquid guiding material member, wherein, the porous liquid guiding material member has a plurality of outer surfaces, and the heating member is provided on at least two adjacent outer surfaces of the plurality of outer surfaces to form at least two heating surfaces; the porous liquid guiding material member has at least one outer surface that is not provided with the heating member; the heating member forms one or more metal heating trajectories on the heating surfaces, and the metal heating trajectory is rectangular wave-shaped;

the porous liquid guiding material member is capable of realizing a liquid transmission along a lengthwise direction which is defined as a first direction, and an airflow transmission along a second direction which is perpendicular to the second direction; each of the heating surfaces directly faces the direction in which the airflow flows to the porous liquid guiding material member; a central axis passing through the porous liquid guiding material member is provided along the second direction, and each of the heating surfaces is axisymmetric along the central axis.

2. The three-dimensional atomization device for heating a porous liquid guiding material according to claim 1, wherein the rectangular wave-shaped metal heating trajectory is composed of main heating sections, a top connecting section and a bottom connecting section; a plurality of the main heating sections are parallel; the top connecting section is used to connect top ends of two adjacent main heating sections; the bottom connecting section is used to connect bottom ends of two adjacent main heating sections.

3. The three-dimensional atomization device for heating a porous liquid guiding material according to claim 2, wherein among the plurality of the main heating sections of the metal heating trajectory, every two adjacent main heating sections are equidistantly distributed.

4. The three-dimensional atomization device for heating a porous liquid guiding material according to claim 2, wherein among the plurality of the main heating sections of the metal heating trajectory, sectional areas of the main heating sections are stepped or progressive gradually increasing or decreasing from two sides toward a center.

5. The three-dimensional atomization device for heating a porous liquid guiding material according to claim 1, wherein the porous liquid guiding material member is provided with a hollow flow-through hole in the lengthwise direction, and the liquid to be atomized flows through the flow-through hole;

alternatively, the porous liquid guiding material member is provided with an inwardly recessed strip groove in the lengthwise direction, and the liquid to be atomized flows through the strip groove.

6. The three-dimensional atomization device for heating a porous liquid guiding material according to claim 1, wherein a section of the porous liquid guiding material member in a width direction is rectangular.

7. The three-dimensional atomization device for heating a porous liquid guiding material according to claim 1, wherein the three-dimensional atomization device for heating a porous liquid guiding material further comprises an outer cover and a base; the base covers an opening at one end of the outer cover, and is provided with an air inlet communicating with the inside of the outer cover; the outer cover is provided with an aerosol outlet on the top; an airflow channel is provided between the air inlet and the aerosol outlet;

the porous liquid guiding material member and the heating member are provided in the outer cover; the porous liquid guiding material member is fixed on the base; the porous liquid guiding material member and the heating member are located in the airflow channel; the heating member has a positive terminal and a negative terminal; the base is provided thereon with a first electrode electrically connected with the positive terminal of the heating member and a second electrode electrically connected with the negative terminal of the heating member.

8. The three-dimensional atomization device for heating a porous liquid guiding material according to claim 7, wherein two ends of the porous liquid guiding material member are each fixedly provided with a silicone member, and the silicone member is provided with an annular groove;

the base is provided thereon with a first convex post facing the porous liquid guiding material member; a cover is provided above the porous liquid guiding material member; the cover is provided with a second convex post facing the porous liquid guiding material member; the first convex post and the second convex post are respectively clamped into the groove of the silicone member.

9. The three-dimensional atomization device for heating a porous liquid guiding material according to claim 8, wherein two ends of the porous liquid guiding material member are respectively provided with an annular protrusion; the silicone member is provided therein with an annular receiving groove; the annular protrusion is clamped in the receiving groove of the silicone member.

10. The three-dimensional atomization device for heating a porous liquid guiding material according to claim 8, wherein the cover is provided with a through hole and a silicone cover; the silicone cover is provided with a connection hole extending outward; the connection hole communicates with the aerosol outlet of the outer cover.

11. The three-dimensional atomization device for heating a porous liquid guiding material according to claim 5, wherein a section of the porous liquid guiding material member in a width direction is triangular, trapezoidal or rectangular.

* * * * *